United States Patent
Abraham et al.

[11] Patent Number: 5,999,687
[45] Date of Patent: Dec. 7, 1999

[54] APPARATUS AND METHOD FOR DELIVERING $CO_2$ LASER ENERGY

[75] Inventors: Martin Abraham, Hod Hasharon; Ytzhak Rozenberg, Ramat Gan; Nisim Hay, Tel Aviv, all of Israel

[73] Assignee: Laser Industries Limited, Tel Aviv, Israel

[21] Appl. No.: 08/966,064

[22] Filed: Nov. 10, 1997

[30] Foreign Application Priority Data

Nov. 10, 1996 [IL] Israel ......................................... 119593

[51] Int. Cl.⁶ ................. G02B 6/32; A61C 1/00
[52] U.S. Cl. ................. 385/902; 385/33; 433/29
[58] Field of Search ................. 433/29; 385/902, 385/33, 119

[56] References Cited

U.S. PATENT DOCUMENTS

| | | | |
|---|---|---|---|
| 4,848,859 | 7/1989 | Nagasawa | 362/32 |
| 4,919,505 | 4/1990 | Bartosiak et al. | 350/96.18 |
| 5,151,029 | 9/1992 | Levy | 433/29 |
| 5,325,458 | 6/1994 | Morrow et al. | 385/125 |
| 5,738,678 | 4/1998 | Patel | 606/10 |
| 5,759,031 | 6/1998 | Goldsmith et al. | 433/29 |

*Primary Examiner*—Rodney Bovernick
*Assistant Examiner*—Victoria D. Hao
*Attorney, Agent, or Firm*—Friedman Siegelbaum LLP

[57] ABSTRACT

A system for delivering a $CO_2$ laser beam to the roots of a tooth is provided. The system includes a laser beam source, a first fiber having a first diameter connected to the laser beam source at its proximal end and to a hand piece at its distal end, the hand piece including an optical assembly operative to transfer the beam from the distal end of the first fiber to the proximal end of a second fiber having a second diameter smaller than the first diameter with substantial power loss.

33 Claims, 2 Drawing Sheets

1

APPARATUS AND METHOD FOR DELIVERING $CO_2$ LASER ENERGY

FIELD OF THE INVENTION

The present invention relates to apparatus and method for delivering a $CO_2$ laser beam generally and more particularly to apparatus and method for delivering a $CO_2$ laser beam which is particularly useful for the class of dental procedures known as root canal procedures.

BACKGROUND OF THE INVENTION

In certain dental applications, it is advisable to perform root canal procedures after drilling the tooth to the root. At present, any infection occurring after the root cavity treatment is usually dealt with by a course of antibiotics. Treatment with antibiotics is not local and also delays the continuation of the treatment after the root cavities have been made since the effect of the antibiotics is not immediate.

SUMMARY OF THE INVENTION

It is an object of the present invention to provide a system and method for local sterilization of the drilled-out interior of the root of a tooth by the application of a laser beam.

According to one aspect of the present invention a low power $CO_2$ laser beam applied to the root itself through the drilled cavity prevents infection caused by contamination during the drilling process.

There is thus provided, in accordance with a further aspect of the present invention, a fiber based delivery system terminating in a short tapered fiber cone whose dimensions are small enough to be inserted into the drilled cavity such that the distal end of the fiber lies close to or within the root of the tooth.

Still further, there is provided according to yet another aspect of the present invention, an optical relay system between the master delivery fiber and the tapered cone. In this way, the delivery of at least 2 watts and up to 4 watts of power can be achieved without the fiber tip heating up by more than about 5° C. In this way laser delivery to the root of the tooth can be achieved without effectively raising the temperature of the body of the tooth itself.

There is provided, in accordance with an aspect of the present invention, a system for delivering a laser beam to the roots of the tooth. The laser beam is a $CO_2$ beam. The system includes a laser beam source, a first fiber having a first diameter connected to the laser beam source in its proximal end and to a hand piece in its distal end, the hand piece including an optical assembly operative to transfer the beam from the distal end of the first fiber to the proximal end of a second fiber having a second diameter smaller than the first diameter with substantial power loss.

Furthermore, in accordance with an embodiment of the present invention, the hand piece includes a relay lens facing the distal end of the first fiber, and an aperture stop for transferring a portion of the laser beam to the proximal end of the second fiber.

Still further, there is provided according to yet another embodiment of the present invention, a system for delivering a $CO_2$ laser beam which includes a laser beam source, a first fiber having a first diameter connected to the laser beam source in its proximal end and to a hand piece in its distal end, the hand piece including an optical assembly operative to transfer the beam from the distal end of the first fiber to a the proximal end of a second fiber having a second diameter smaller than the first diameter with substantial power loss.

In addition, in accordance with an embodiment of the present invention, the hand piece includes a relay lens facing the distal end of the first fiber, an aperture stop for transferring a portion of the laser beam to the proximal end of the second fiber, whereby the quality of the beam entering the second fiber is improved, minimizing thermal damage to the tooth.

Furthermore, in accordance with an embodiment of the present invention, the system further includes a reflecting element disposed intermediate the aperture and the proximal end of the second fiber for deflecting the laser beam to the second fiber. The second diameter of the second fiber is small enough to allow insertion of the second fiber into the roots of a tooth.

Furthermore, the second fiber is disposable and the first and second fiber does not substantially heat up during operation. The angle between the hand piece and the second fiber is 110 degrees.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE PREFERRED EMBODIMENT

Figure 1:
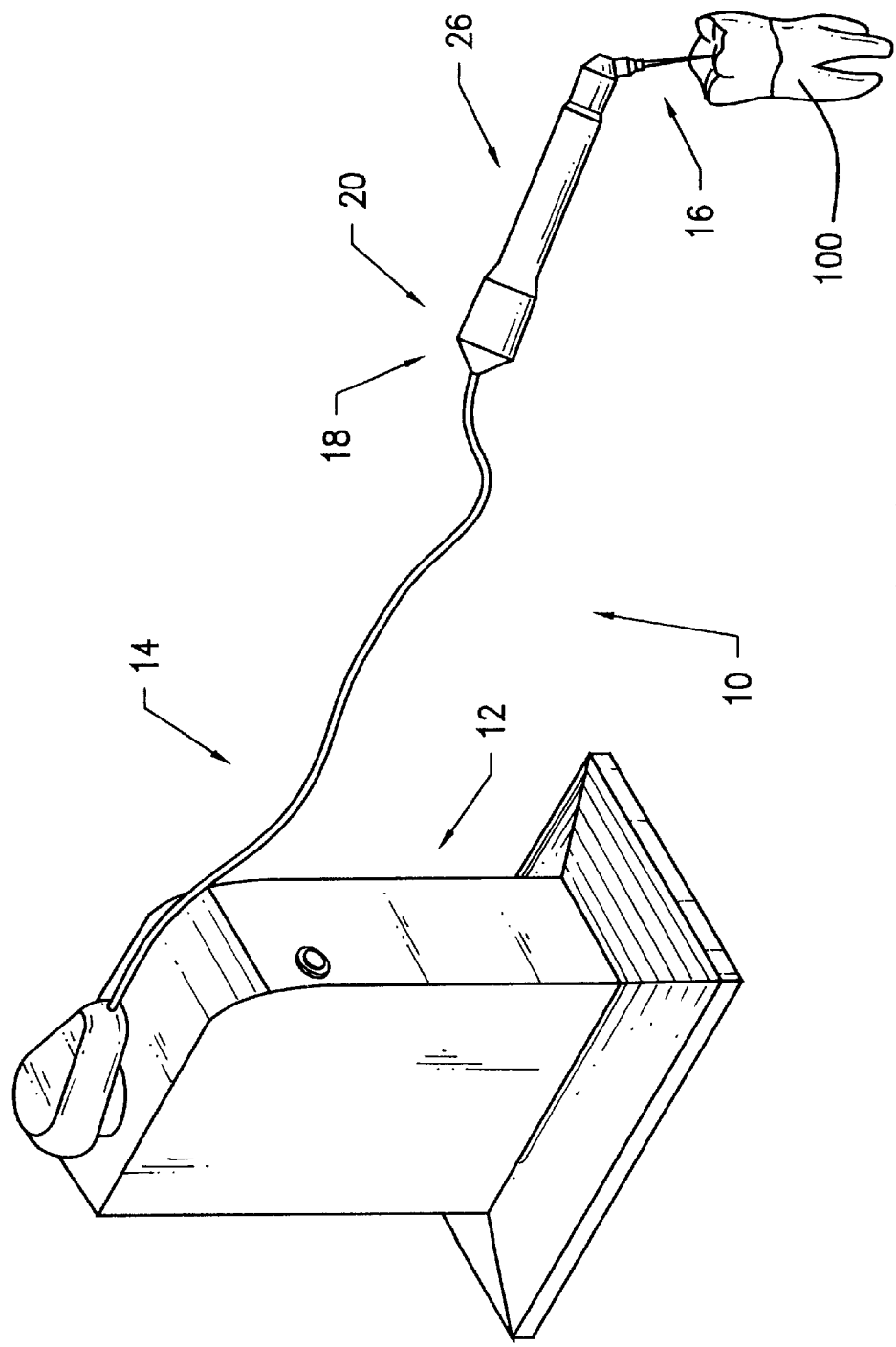
FIG. 1 is a pictorial illustration of a system for delivering a $CO_2$ laser beam, constructed and operative in accordance with a preferred embodiment of the present invention.
Figure 2:
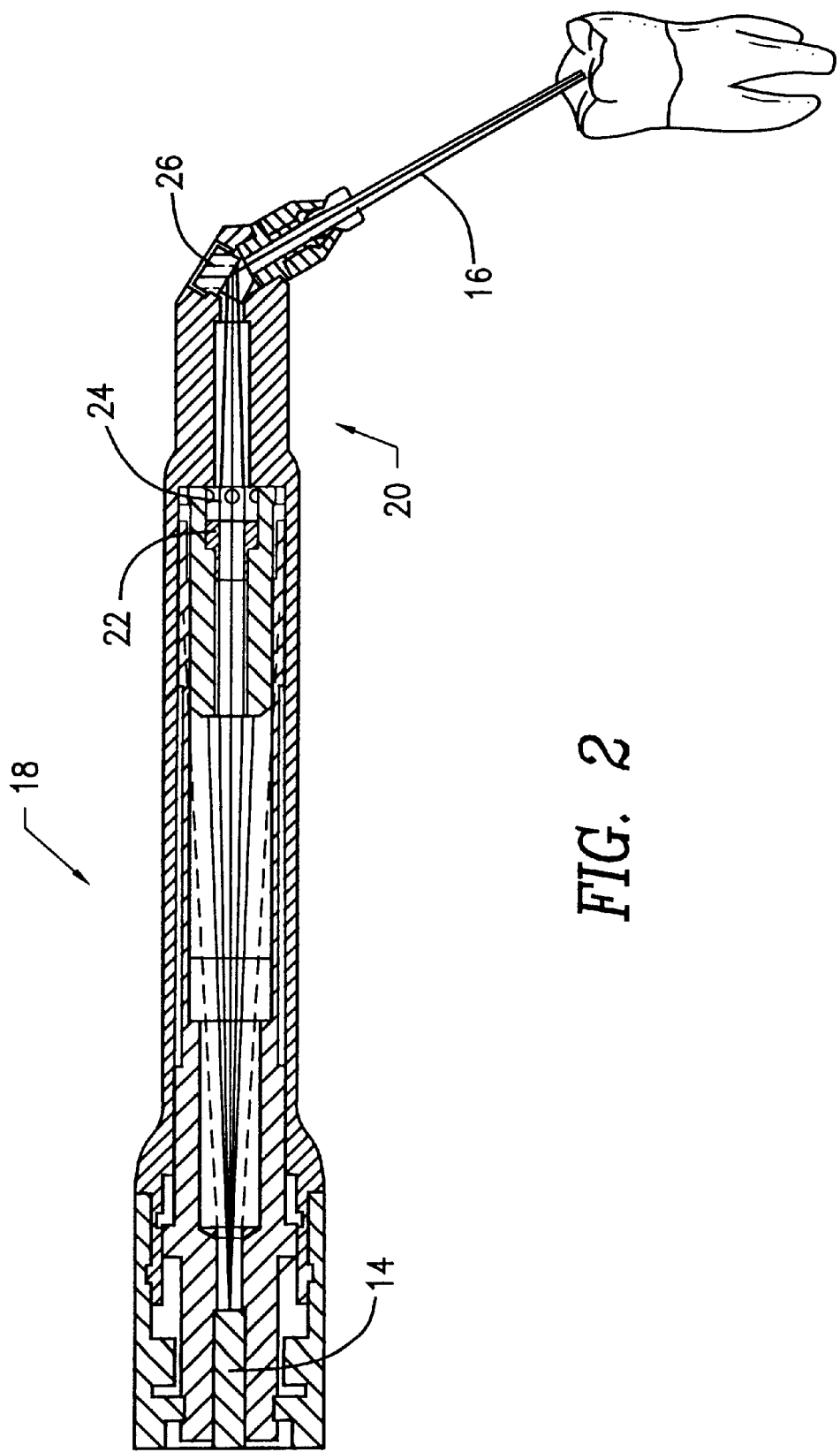
FIG. 2 is an illustration of the hand piece of the system of FIG. 1.
Figure 2:
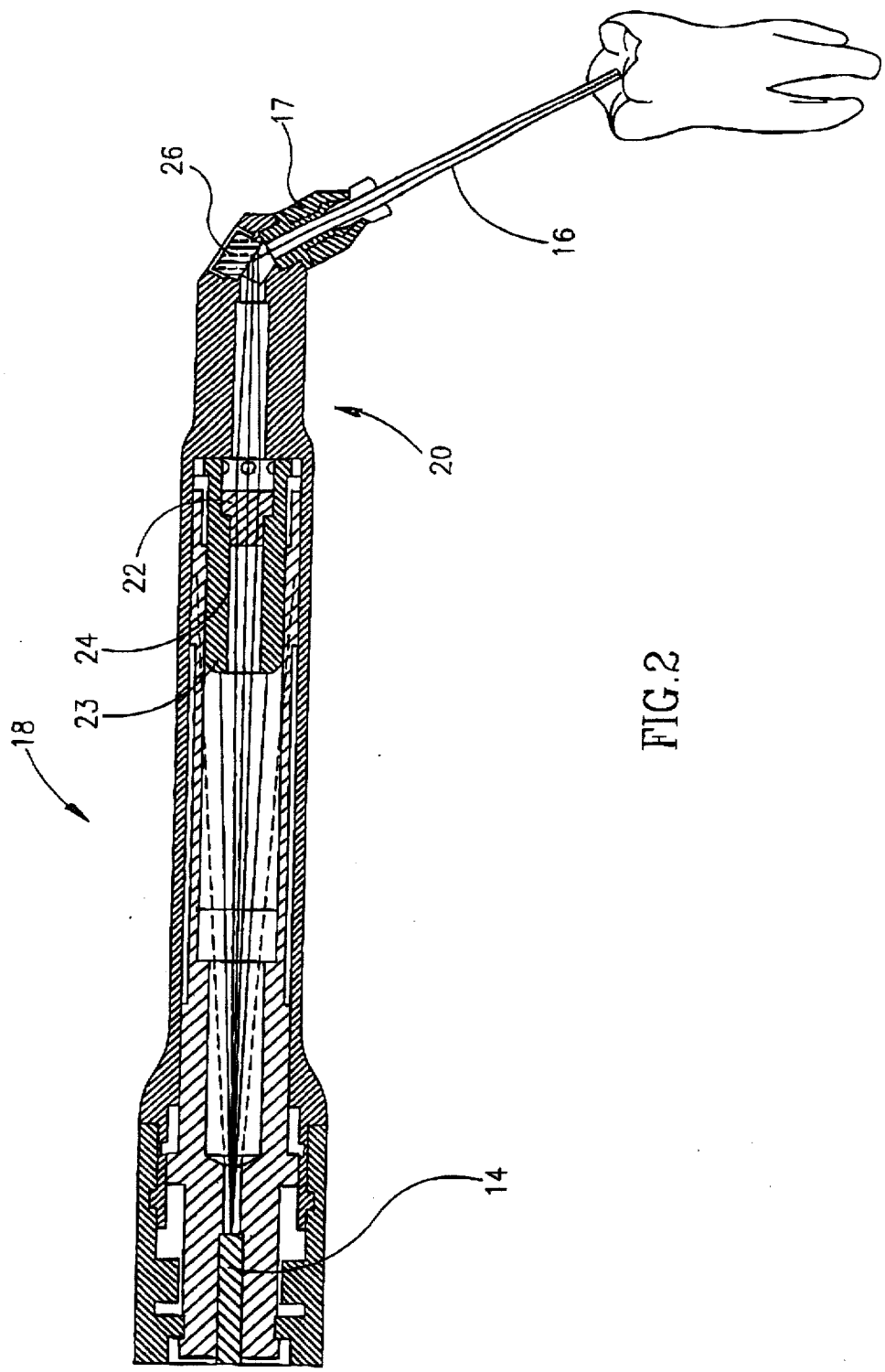

Reference is now made to FIGS. 1 and 2 which illustrate the laser delivery system, generally referenced 10, of the present invention. Laser delivery system 10 comprises a $CO_2$ laser source 12 coupled to a master fiber delivery system 14. Master fiber 14 is coupled to a short conical tapered fiber 16 via a chuck 17 of the hand piece 18. The hand piece 18 includes an optical assembly 20 including a relay lens 22, held in the optical assembly 20 by an aperture stop 23 with an aperture 24 extending therethrough and deflecting mirror 26. In the preferred embodiment fiber 16 is operative to deliver a $CO_2$ laser beam to the roots of a tooth 100 in order to prepare the tooth after root cavities have been made.

In its preferred, but non limiting operation, laser delivery system 10 is used for pre-root canal procedures, such as sterilizing the root cavities or drying the root cavities prior to root canal procedures.

In the illustrated embodiment, $CO_2$ laser 12 is coupled to the hollow silver master fiber 14 having a length of about 1 meter to enable the dentist to operate conveniently. In the preferred embodiment, the fibers and a hollow silver waveguide with dielectric coating disclosed in U.S. Pat. No. 5,325,458 to Morrow et al. incorporated herein by reference. Alternatively, any other type of fiber conducting $CO_2$ laser radiation may be used, for example hollow teflon silver coated fiber or solid silver halide fiber, all well known in the art.

Handpiece 18 comprises a system of holding and centering the master fiber 14 a certain distance from the relay lens 22. The image of the end of the master fiber 14 is focused onto the entry port of the short tapered fiber 16. Between the lens and the tapered fiber (taper) 16 there is a deflecting mirror 26 which creates a convenient 110 degrees between the axis of the master fiber 14 and the axis of the tapered fiber 16 to facilitate work on teeth.

A particular feature of the present invention is that it provides a low power transfer of the laser beam from fiber 14 to fiber 16.

Since most fiber delivery systems for $CO_2$ lasers have large numerical aperture outputs due to imperfections in the surface quality of the fiber, the exit angle of the fiber is always greater than the input angle. For the present system, a non-limiting example of a 1 meter length hollow silver fiber 14 of 1 mm internal diameter has an exit numerical aperture of 0.06 whereas the input numerical aperture from the laser is only 0.03.

The end of the fiber 14 has to be imaged onto the entrance surface of a tapered fiber 16. The dimensions of the tapered fiber can be internal diameter from 0.7 to 0.3 mm over a length of about 20 mm with an outside diameter at the distal end of about 0.45 mm since fiber 16 is preferably disposable and is entered into the roots of a tooth.

The optical assembly 20 of handpiece 18 is designed to bridge the above differences. In the preferred embodiment, the relay lens 22 used in the handpiece images the 1 mm exit face of the master fiber 14 to an image size of 0.4 mm. Then, in this way all the rays forming a focus after the deflecting mirror 26 will be perfectly coupled into the 0.7 mm inside diameter of the tapered fiber 16.

Since the numerical aperture of the master fiber 14 is 0.06 (3.5° half angle) then after the relay lens the numerical aperture entering the taper 16 will be 0.15. (To increase power transfer of the taper 16 itself it is desirable that the numerical aperture of the cone of rays entering the taper be as small as possible.) With larger numerical apertures, the power transfer of the taper 16 itself is lower and this power loss manifests itself in a very large rise in temperature. In such a case, the taper 16 becomes very hot and would cause thermal damage to the inside of the tooth.

It is therefore desirable to aperture the beam before it strikes the input surface of the tapered fiber. Such aperturing will not affect the size of the focused beam at the entrance surface of the taper but will reduce the numerical aperture of entrance beam. In this way, the power transfer of The taper itself will increase. The overall power transfer of the handpiece will, however, be reduced by this technique. However, with this procedure for root canals only about up to 4 watts of power need to be delivered by the taper. In the present laser system, the maximum output power of the master fiber 14 is 15 watts.

Table 1 below shows results of power transfer of the taper itself as a function of size of aperture with corresponding numerical aperture entrance to the taper. The power transferred from the end of the master fiber through the pinhole is also indicated.

TABLE

| A<br>Pinhole Diameter<br>Aperture (mm.) | B<br>Input Numerical<br>Aperture to Taper | C<br>Power<br>Transferred<br>by Pinhole | D<br>Power Transfer<br>of Taper Itself |
| --- | --- | --- | --- |
| 8 | 0.15 | 100% | 68.8% |
| 6 | 0.11 | 96.9% | 69.4% |
| 5 | 0.09 | 87.5% | 73.2% |
| 4 | 0.076 | 71.9% | 78.3% |
| 3 | 0.057 | 51.6% | 81.0% |
| 2 | 0.038 | 26.6% | 88% |

As can be seen from the table, the overall power transfer of the handpiece [pinhole transfer×power transfer of taper 16 itself] is greater for a pinhole diameter of 8 mm. than for one of 2 mm. However, the power transfer of the taper 16 itself is greatest with the 2 mm. aperture, resulting in the minimum amount of heat buildup in the taper itself. This effect, as already explained, is very desirable and in our system we chose an aperture diameter of 3.5 mm. In the actual handpiece design as shown in FIG. 2 the inside diameter effectively blocks all rays emitted from the master fiber 14 such that after the relay lens 22 the numerical aperture entering the taper does not exceed 0.066.

That is, all rays that would have entered the taper at a numerical aperture greater than 0.066 have been blocked.

While the foregoing description and drawings represent the preferred embodiments of the present invention, it will be understood that various changes and modifications may be made without departing from the spirit and scope of the present invention. For example, fiber 14 may be replaced by a multiple-section light-guide or be at other desirable length. Another example is that for each tooth the length of fiber 16 may be adjusted. Further, fiber 16 may be marked so that the dentist can know the depth of penetration.

It will be further appreciated that the present invention is not limited by what has been described hereinabove and that numerous modifications, all of which fall within the scope of the present invention, exist. Rather the scope of the invention is defined by the claims which follow:

We claim:

1. Apparatus for drying and sterilizing the interior of a cavity comprising:

a handpiece having a proximal end and a distal end, a first optic fiber for transmitting laser energy from a source of laser energy to said handpiece, the first optic fiber having a first diameter, and having a proximal end coupled to the source and a distal end coupled to the proximal end of said handpiece, a second optic fiber in operative communication with said first optic fiber, said second optic fiber having a second diameter smaller than said first diameter and having a proximal end within said distal end of said handpiece and a distal end protruding from said distal end of said handpiece for insertion into the cavity, and said handpiece including a transmission path configured for the transmission of laser energy from said first optic fiber to said second optic fiber and a beam limiter along said transmission path intermediate said first optic fiber and said second optic fiber, for reducing the divergence angle of said transmitted laser beam from said first optic fiber to said second optic fiber.

2. The apparatus of claim 1, wherein said transmission path is configured to permit the transmission of laser energy with a substantial power loss.

3. The apparatus of claim 1, additonally comprising a relay lens along said transmission path, said relay lens in operative communication with said first and second optic fibers for transferring a portion of said transmitted laser energy to said second optic fiber.

4. The apparatus of claim 3, wherein said handpiece includes a longitudinal axis and said first optic fiber, said beam limiter and said relay lens are substantially coaxial along said longitudinal axis.

5. The apparatus of claim 4, wherein said second fiber includes a longitudinal axis extending therethrough, and is adapted for receipt in said handpiece, such that when in said handpiece said longitudinal axis of said second fiber is at a first angle with respect to said longitudinal axis of said handpiece.

6. The apparatus of claim 5, wherein said handpiece additionally comprises, a mirror in operative communication with said first optic fiber and said second optic fiber, said mirror at a second angle with respect to said longitudinal axis of said handpiece, said second angle to allow for reflecting laser energy to said second optic fiber.

7. The apparatus of claim 5, wherein said first angle is approximately 110 degrees.

8. The apparatus of claim 1, additionally comprising a source of laser energy.

9. The apparatus of claim 8, wherein said source of laser energy produces at least 12 watts of power.

10. The apparatus of claim 8, wherein said source of laser energy is a $CO_2$ laser.

11. The apparatus of claim 1, wherein said second optic fiber includes a tapered fiber, tapered inward from said proximal end to said distal end.

12. The apparatus of claim 1, wherein said handpiece comprises a releasable portion, said releasable portion for holding said second optic fiber.

13. The apparatus of claim, 12, wherein said second optic fiber includes a tapered fiber, tapered inward from said proximal end to said distal end.

14. The apparatus of claim 1, wherein said beam limiter includes an aperture stop, with an aperture extending at least substantially therethrough.

15. A method of treating a human tooth comprising the steps of:
   providing a source of laser energy in communication with a handpiece, said handpiece including a first optic fiber for receiving said laser energy from said source of laser energy, a second optic fiber in operative communication with said first optic fiber and transmission path intermediate said first and second optic fibers, said transmission path configured for reducing the power of said laser energy transmitted from said first optic fiber to said second optic fiber;
   drilling out a cavity in said tooth;
   drying and sterilizing the interior of said cavity by inserting said second optic fiber into said cavity and actuating said source of laser energy.

16. The method of claim 15, additionally comprising the step of:
   drilling longitudinally through a root of the tooth.

17. The method of claim 15, additionally comprising the step of:
   filling the cavity.

18. The method of claim 15, wherein said power reduction is such that is sufficient that when a source of at least 12 watts is used the power transmitted to the interior of the cavity is not greater than 5 watts.

19. The method of claim 15, additionally comprising the step of: disposing of said second optic fiber and replacing it with a new one prior to subsequent repetition of the method.

20. The method of claim 15, wherein in the providing step the source of laser energy provided includes a $CO_2$ laser.

21. A system for drying and sterilizing the interior of a cavity comprising:
   a source of laser energy;
   a handpiece having a proximal end and a distal end;
   a first optic fiber for transmitting laser energy from said source of laser energy to said handpiece, the first optic fiber having a first diameter, and having a proximal end coupled to the source and a distal end coupled to the proximal end of said handpiece;
   a second optic fiber in operative communication with said first optic fiber, said second optic fiber having a second diameter smaller than said first diameter and having a proximal end within said distal end of said handpiece and a distal end protruding from said distal end of said handpiece for insertion into the cavity; and
   said handpiece further including a transmission path configured for the transmission of laser energy from said first optic fiber to said second optic fiber and a beam limiter along said transmission path intermediate said first optic fiber and said second optic fiber, for reducing the divergence angle of said transmitted laser beam from said first optic fiber to said second optic fiber.

22. The system of claim 21, wherein said transmission path is configured to permit the transmission of laser energy with a substantial power loss.

23. The system of claim 21, additionally comprising a relay lens along said transmission path, said relay lens in operative communication with said first and second optic fibers for transferring a portion of said transmitted laser energy to said second fiber.

24. The system of claim 23, wherein said handpiece includes a longitudinal axis and said first optic fiber, said beam limiter and said relay lens are substantially coaxial along said longitudinal axis.

25. The system of claim 24, wherein said second fiber includes a longitudinal axis extending therethrough, and is adapted for receipt in said handpiece, such that when in said handpiece said longitudinal axis of said second fiber is at a first angle with respect to said longitudinal axis of said handpiece.

26. The system of claim 25, wherein said handpiece additionally comprises, a mirror in operative communication with said first optic fiber and said second optic fiber, said mirror at a second angle with respect to said longitudinal axis of said handpiece, said second angle to allow for reflecting laser energy to said second optic fiber.

27. The system of claim 25, wherein said first angle is approximately 110 degrees.

28. The system of claim 21, wherein said source of laser energy is a $CO_2$ laser.

29. The system of claim 21, wherein said second optic fiber includes a tapered fiber, tapered inward from said proximal end to said distal end.

30. The system of claim 21, wherein said handpiece comprises a releasable portion, said releasable portion for holding said second optic fiber.

31. The system of claim 30, wherein said second optic fiber includes a tapered fiber, tapered inward from said proximal end to said distal end.

32. The system of claim 21, wherein said beam limiter includes an aperture stop, with an aperture extending at least substantially therethrough.

33. The system of claim 21, wherein said source of laser energy produces at least 12 watts of power.

* * * * *

UNITED STATES PATENT AND TRADEMARK OFFICE
CERTIFICATE OF CORRECTION

PATENT NO. : 5,999,687
DATED : December 7, 1999
INVENTOR(S) : Abraham, Martin et al.

It is certified that error appears in the above-identified patent and that said Letters Patent is hereby corrected as shown below:

Title page,
Please replace the figure with the figure shown below.

Please replace Fig. 2 with the figure attached.

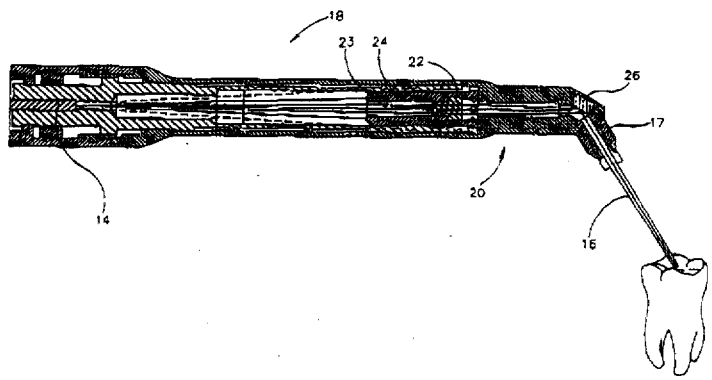

Signed and Sealed this

Twenty-sixth Day of February, 2002

Attest:

JAMES E. ROGAN
Attesting Officer  Director of the United States Patent and Trademark Office